(12) United States Patent
Stolyarenko

(10) Patent No.: US 6,176,853 B1
(45) Date of Patent: Jan. 23, 2001

(54) FOOT SWITCH TO PROPORTIONALLY CONTROL A MEDICAL CUTTING DEVICE

(75) Inventor: Georgie E. Stolyarenko, Moscow (RU)

(73) Assignee: Scieran Technologies, Inc., Laguna Hills, CA (US)

( * ) Notice: Under 35 U.S.C. 154(b), the term of this patent shall be extended for 0 days.

(21) Appl. No.: 09/186,570

(22) Filed: Nov. 5, 1998

(51) Int. Cl.$^7$ .................................................. A61B 17/00
(52) U.S. Cl. .............................. 606/1; 606/166; 606/167
(58) Field of Search .................. 74/512, 594.4; 606/166, 167, 1; 251/295

(56) References Cited

U.S. PATENT DOCUMENTS

| | | | |
|---|---|---|---|
| 4,168,707 | * | 9/1979 | Douvas et al. ...................... 128/276 |
| 4,523,911 | * | 6/1985 | Braetsch et al. ...................... 433/101 |
| 4,837,857 | * | 6/1989 | Scheller et al. ...................... 455/617 |
| 4,965,417 | * | 10/1990 | Massie ................................ 200/86.5 |
| 5,271,379 | * | 12/1993 | Phan et al. ............................. 128/4 |
| 5,465,633 | * | 11/1995 | Bernloehr .............................. 74/512 |
| 5,787,760 | * | 8/1998 | Thorlakson ............................ 74/512 |
| 5,916,330 | * | 6/1999 | Jacobson ............................... 74/512 |

* cited by examiner

Primary Examiner—Linda C. M. Dvorak
Assistant Examiner—Jocelyn Debra Ram
(74) Attorney, Agent, or Firm—Irell & Manella LLP

(57) ABSTRACT

A medical system that includes a foot pedal which can be used to actuate a surgical instrument. The surgical instrument may be coupled to an actuator assembly and inserted into a cornea. The actuator assembly may be coupled to the foot pedal by a cable. The foot pedal may include a platform that can be depressed by a surgeon to move the cable and actuate the surgical instrument.

34 Claims, 5 Drawing Sheets

FOOT SWITCH TO PROPORTIONALLY CONTROL A MEDICAL CUTTING DEVICE

BACKGROUND OF THE INVENTION

1. Field of the Invention

The present invention relates to a foot pedal that can be used to manually actuate a surgical instrument that is inserted into an eye.

2. Background Information

There have been developed various surgical procedures for correcting eye defects. Ophthalmic procedures are typically performed with a surgical instrument that is inserted through an incision in the eye. By way of example, there have been developed guillotine cutters that can cut tissue within the eye. A guillotine cutter typically includes an inner cannula that slides within an outer cannula. The outer cannula is inserted through an incision in the cornea. The inner cannula severs tissue that is pulled within a port of the outer cannula. The inner cannula is typically driven in a reciprocating manner by an electric motor or pneumatic power.

The cornea may have resilient tissue that cannot be cut with a conventional motor or pneumatically driven guillotine cutter. To cut the resilient material the surgeon may remove the guillotine cutter and insert a manually actuated cutter. The surgeon actuates the cutter with one of his hands. This method of actuation may cause an undesirable movement of the cutter within the eye. The surgeon must therefore be careful not to move the cutter while actuating the same. It would be desirable to provide a manual cutter that can be actuated without introducing an undesirable movement of the cutter.

SUMMARY OF THE INVENTION

One embodiment of the present invention is a medical system that includes a foot pedal which can be used to actuate a surgical instrument. The surgical instrument may be coupled to an actuator assembly and inserted into a eye. The actuator assembly may be coupled to the foot pedal by a cable. The foot pedal may include a platform that can be depressed by a surgeon to move the cable and actuate the surgical instrument.

DETAILED DESCRIPTION

Figure 1:
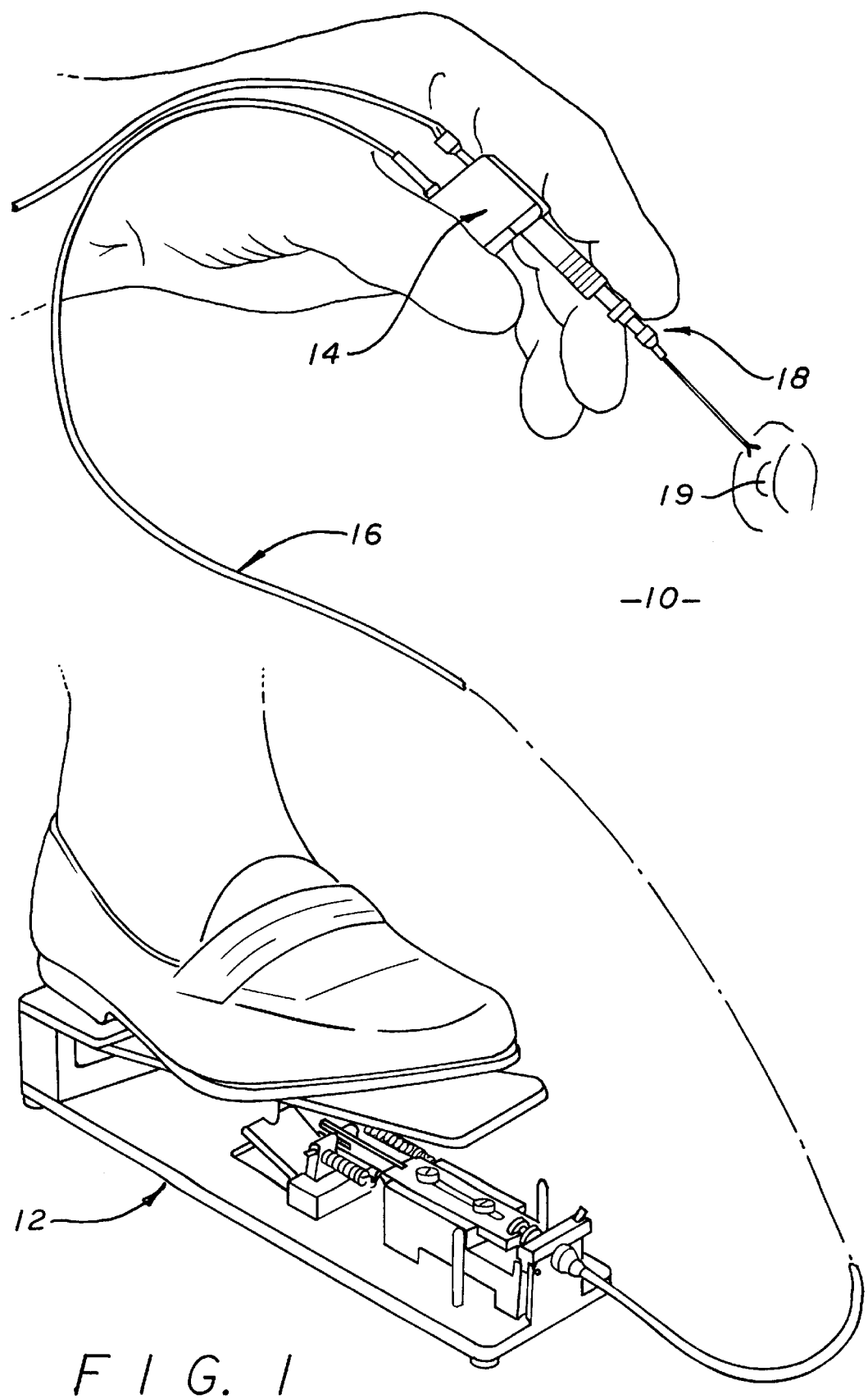
FIG. 1 is an exploded perspective view of a medical system to manually control a surgical instrument.

Referring to the drawings more particularly by reference numbers, FIG. 1 shows an embodiment of a medical system 10 that can manually and proportionally control a surgical instrument. The system 10 includes a foot pedal 12 that is connected to an actuator assembly 14 by a cable 16. The actuator assembly 14 is connected to a surgical instrument 18 that can be inserted into a cornea 19. The foot pedal 12 can be depressed to actuate the surgical instrument 18. The amount of actuation of the instrument 18 can be proportional to the displacement of the foot pedal 12. The system 10 allows a surgeon to actuate the surgical instrument 18 without moving the instrument 18. This improves the reliability of the surgical procedure.

Figure 2:
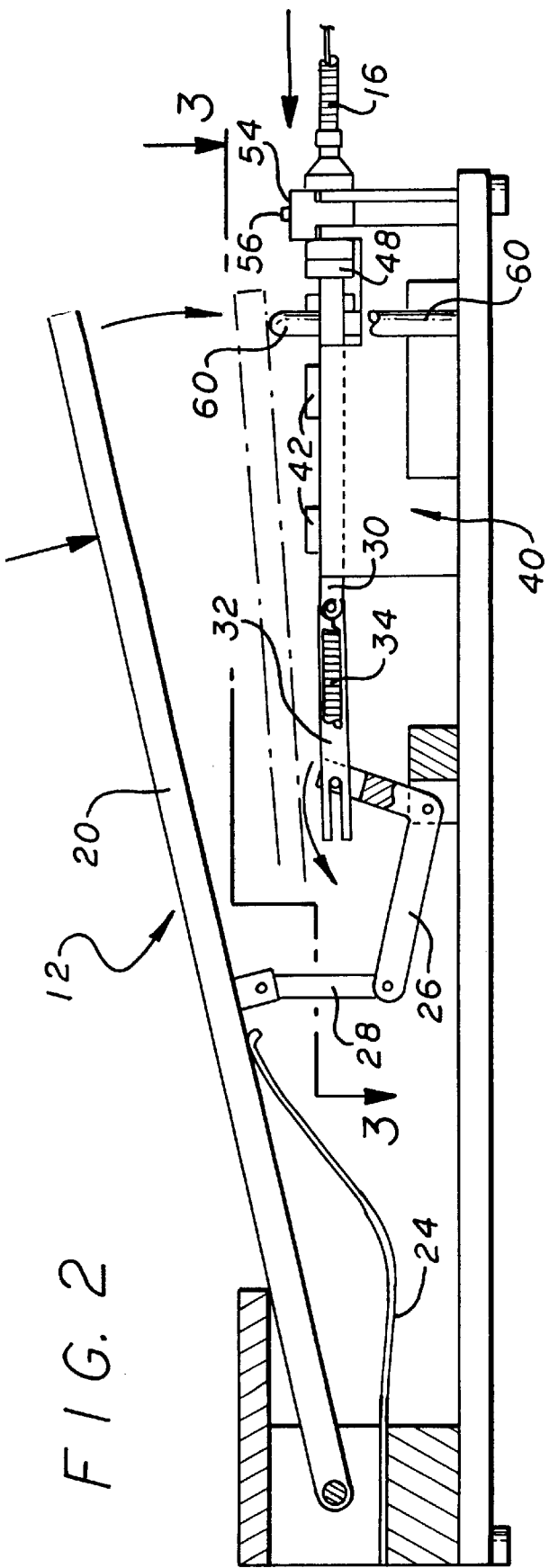
FIG. 2 is a side view of a foot pedal of the system.

As shown in FIG. 2, the foot pedal 12 may include a platform 20 that is pivotally connected to a base plate 22. The platform 20 can be depressed and moved in a downward direction by a surgeon. The platform 20 may be biased into an upward position by a plate spring 24. The spring 24 returns the foot pedal platform 20 to the original rest position when the platform 20 is released by the surgeon. The platform 20 may be coupled to a lever arm 26 by a linkage arm 28. The linkage arm 28 is pivotally connected to the lever arm 26. The lever arm 26 is pivotally connected to the base plate 22.

Figure 3:
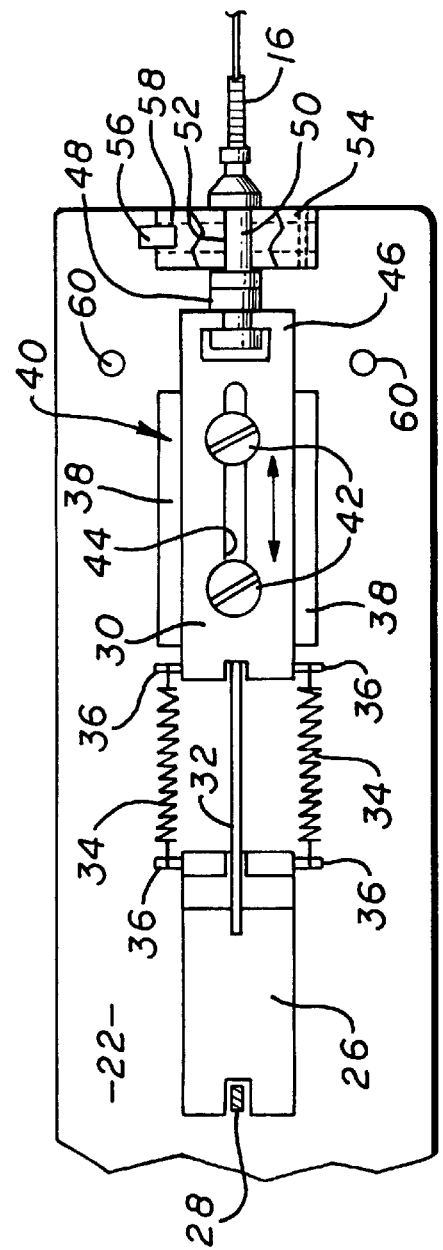
FIG. 3 is a sectional view taken at line 3—3 of FIG. 2.

As shown in FIG. 3, the lever arm 26 is coupled to an actuator plate 30 by an actuator arm 32 and a pair of springs 34. The actuator arm 32 and springs 34 are captured by a pair of pins 36. The springs 34 insure tension between the bracket 26 and actuator plate 30 so that there is proportional movement between the platform 20 and the plate 30.

The actuator plate 30 can slide between two walls 38 of a pedestal 40. The foot pedal 12 may have a pair of screws 42 that extend through a slot 44 of the actuator plate 30 and are attached to the pedestal 40. The screws 42 capture the actuator plate 30 while allowing the plate 30 to move relative to the pedestal 40.

The actuator plate 30 has a C-shaped end 46 which captures a collar 48 of the cable 16. The cable 16 extends through a sleeve 50 that is located within a slot 52 of the pedestal 40. The sleeve 50 can be captured by a locking arm 54 that is pivotally connected to the pedestal 40. The arm 54 can be locked in place by an arcuate shaped spring plate 56 that is attached to the pedestal 40 and engages a bracket slot 58. The cable 16 can be detached from the foot pedal 12 by depressing the spring plate 56, rotating the locking arm 54 in an upward direction, and pulling the sleeve 50 out of the pedestal slot 52.

A surgeon can depress the platform 20 and induce a sliding movement of the actuator plate 30. The movement of the plate 30 pulls the cable 16 and actuates the surgical instrument. The distance that the platform 20 can be depressed may be limited by a pair of pins 60 that extend from the base plate 22.

Figure 4:
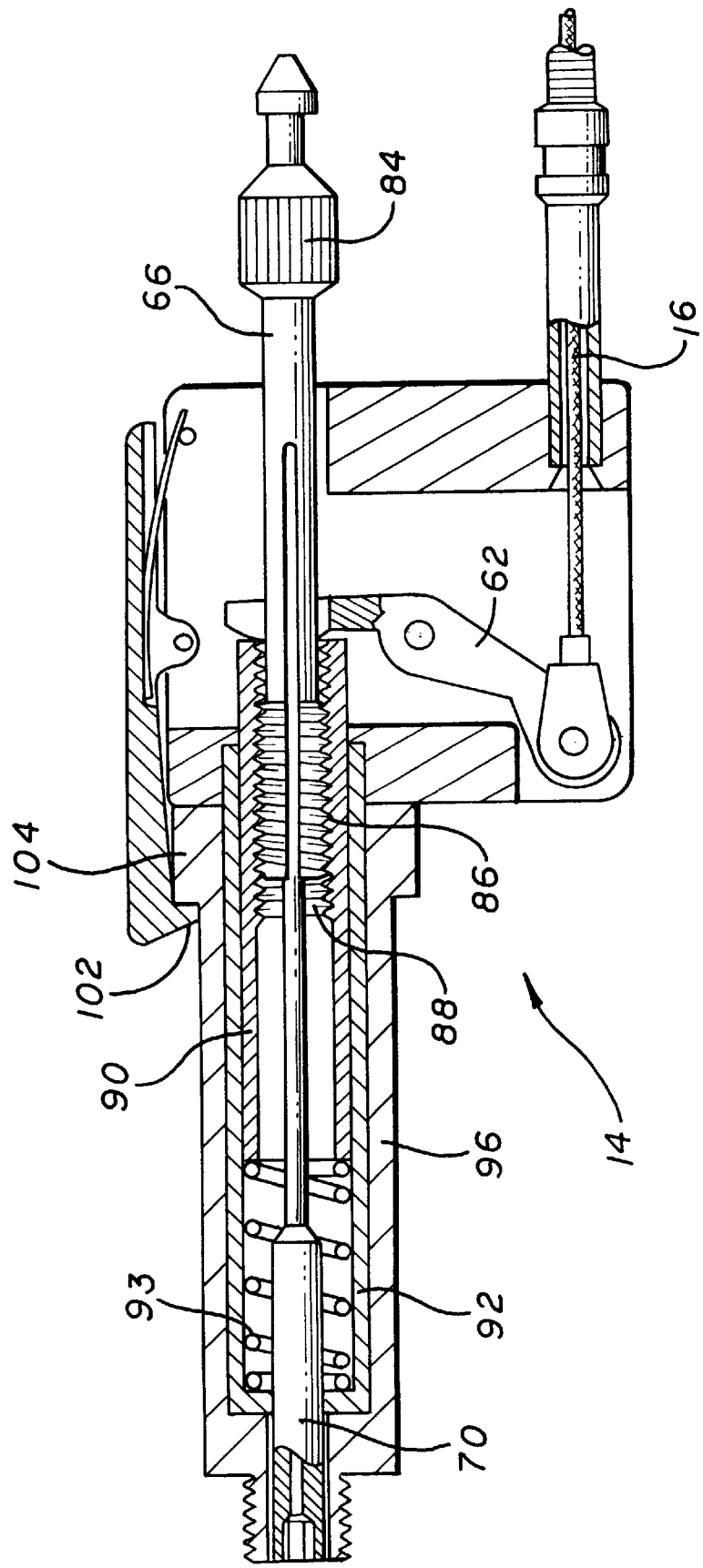
FIG. 4 is a cross-sectional view of an actuator assembly of the system.
Figure 5:
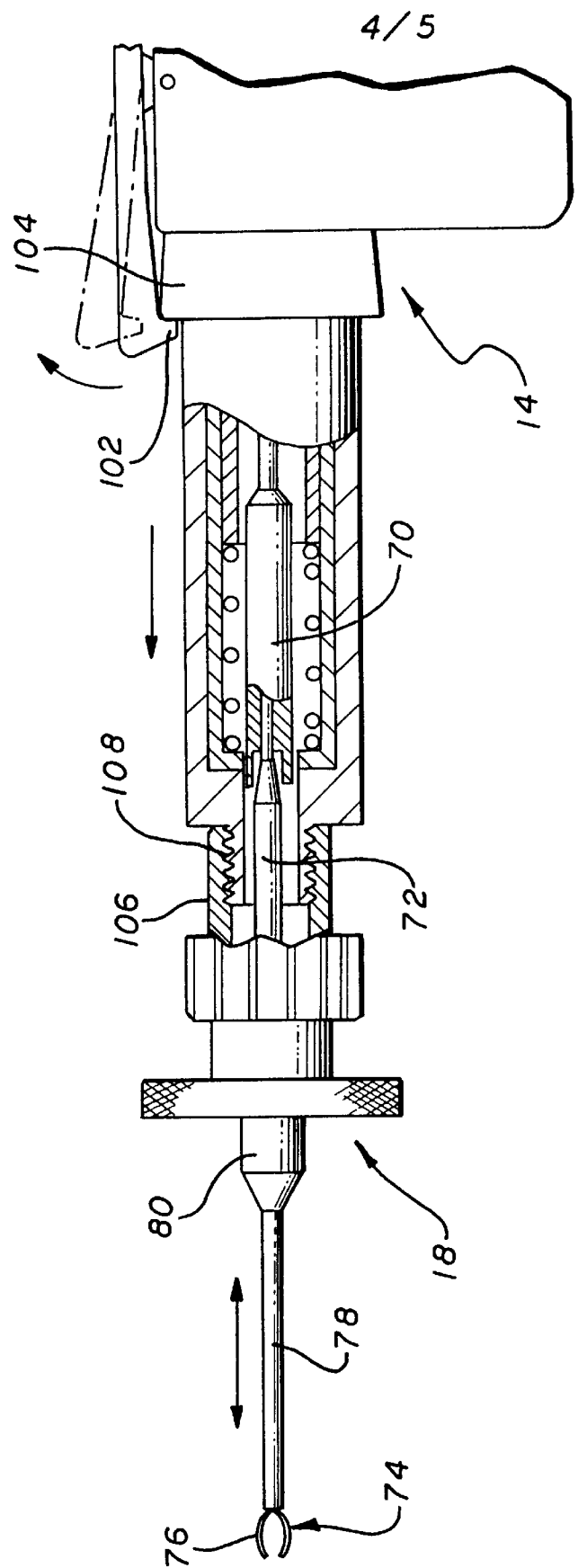
FIG. 5 is a cross-sectional view showing a surgical instrument coupled to the actuator assembly.

Referring to FIGS. 4 and 5, the actuator assembly 14 may include a lever arm 62 that is attached to the cable 16 and pivotally connected to an actuator housing 64. The lever arm 62 is coupled to a rod 66 that extends from the housing 64. The rod 66 includes a plunger portion 70 which engages an actuator rod 72 of the surgical instrument 18. The actuator rod 72 is coupled to an end effector 74 of the instrument 18. Movement of the rods 66 and 72 may actuate the end effector 74.

By way of example, the end effector 74 may be a pair of scissors 76 that are drawn together when a sleeve 78 moves in a distal direction. The sleeve 78 may be coupled to the actuator rod 72. The rod 72 may be coupled to a spring (not shown) that is captured by an instrument housing 80. The spring returns the sleeve 78 back to a proximal position and allows the scissors 76 to expand to the original open position. Although scissors are shown and described, it is to be understood that other types of end effectors 74 may be used in the system 10. For example, the end effector 74 may be a guillotine cutter.

The rod 66 of the actuator assembly 14 may have a knob 84 that can be manipulated by a surgeon to spin the rod 66.

The rod 66 may have an outer threaded portion 86 that screws into a corresponding inner thread 88 of a sleeve 90. Rotation of the knob 84 will translate the rod 66 relative to the sleeve 90 and the housing 64. Translation of the rod 66 varies the rest position of the actuator rod 72 of the instrument 18. By way of example, the surgeon can vary the stroke of a guillotine cutter by rotating the knob 84 and moving the rest position of the rods 66 and 72.

Figure 6:
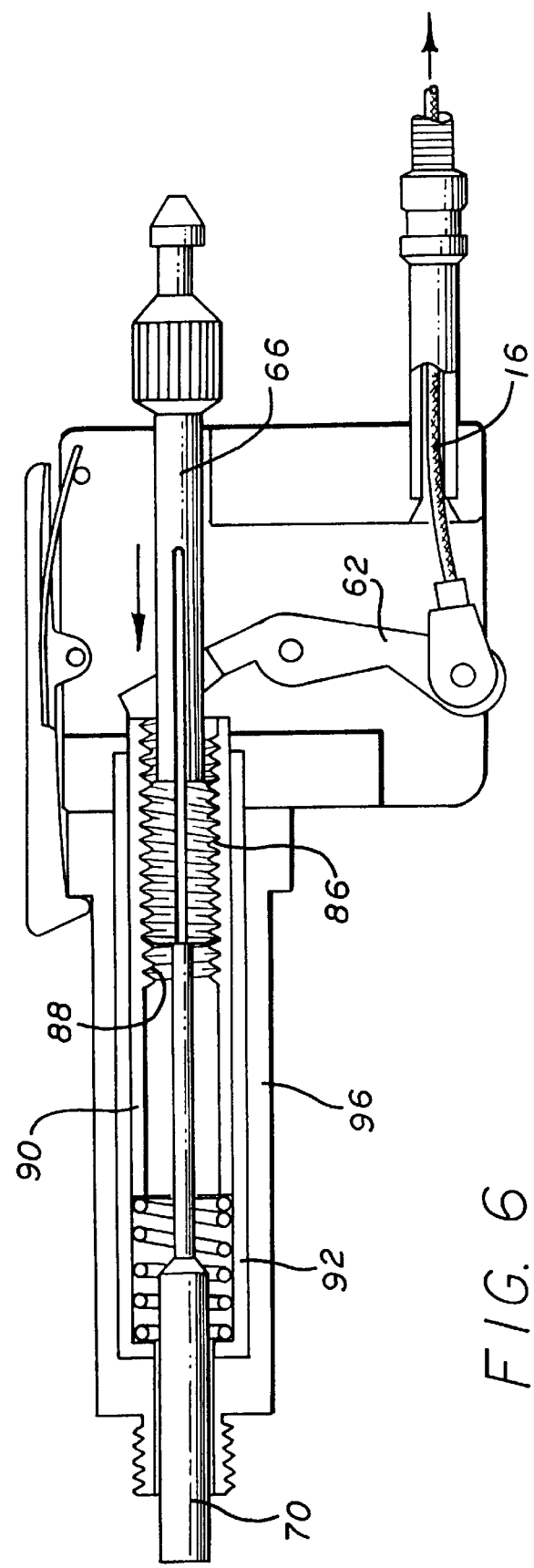
FIG. 6 is a cross-sectional view showing actuation of the actuator assembly.

As shown in FIG. 6, the cable 16 may be pulled to rotate the lever arm 62. The lever arm 62 engages and pushes the sleeve 90 and rod 66 within a barrel portion 92 of the housing 64. Movement of the rod 66 will push the actuator rod 72 and actuate the instrument 18. The barrel 92 may contain a spring 93 that returns the rod 66 to the original position when the foot pedal is released.

As shown in FIGS. 5 and 6, the instrument 18 can be screwed onto an adapter 96 that slides onto the barrel portion 92 of the housing 64. The adapter 96 can be secured to the housing 64 by a spring biased latch 100. The latch 100 has a lip 102 that engages a collar 104 of the adapter 96 to secure the same. The adapter latch 100 is pivotally connected to the housing 64 so that the latch 100 can be depressed and rotated to disengage the lip 102 from the collar 104. The adapter 96 can then be pulled away from the housing barrel 92 so that a new surgical instrument can be attached to the adapter 96 and reassembled to the actuator assembly 14. The instrument housing 80 may have an internal thread 106 that screws onto an external thread 108 of the housing 64 so that the instrument 18 can be readily attached to the actuator assembly 14.

In operation, a surgeon may insert the surgical instrument 18 into an eye. The surgeon can then depress the foot pedal 12 which pulls the cable 16. Pulling the cable 16 rotates the lever arm 62 of the actuator assembly 14. Rotation of the lever arm 62 moves the rods 66 and 72 and actuates the end effector 74 of the instrument 18. The surgeon can vary the speed and amount of actuation by a corresponding manipulation of the foot pedal 12. The foot pedal 12 and actuator assembly 14 may be constructed so that a movement of the instrument actuator rod 72 is proportional to the movement of the foot pedal platform 20. By way of example, this allows a surgeon to closely control the amount of cut created by a cutting instrument.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical system that can allow a surgeon to manually actuate a surgical instrument, comprising:
   an actuator assembly housing;
   an adapter that can couple the surgical instrument to said actuator assembly housing;
   an actuator rod that is coupled to said actuator assembly housing and can be moved to actuate the surgical instrument;
   a cable that is coupled to said actuator rod; and,
   a foot pedal that is coupled to said cable, said foot pedal having a platform which can be moved to move said cable and said actuator rod and actuate the surgical instrument.

2. The medical system of claim 1, wherein the actuation of the surgical instrument is proportional to the movement of said platform.

3. The medical system of claim 1, wherein said foot pedal includes an actuator plate that pulls said cable when said platform is depressed.

4. The medical system of claim 1, wherein said cable includes a collar that is captured by a locking arm of said foot pedal.

5. The medical system of claim 1, wherein said actuator rod has an adjustable rest position.

6. A medical system that can allow a surgeon to manually actuate a surgical instrument, comprising:
   an actuator assembly that can be coupled to the surgical instrument;
   a cable that is coupled to said actuator assembly; and,
   a foot pedal that is coupled to said cable, said foot pedal having a platform which can be moved to move said cable and actuate the surgical instrument, and an actuator plate that pulls said cable when said platform is depressed.

7. The medical system of claim 6, wherein the actuation of the surgical instrument is proportional to the movement of said platform.

8. The medical system of claim 6, wherein said actuator assembly includes an actuator rod that is moved when said cable is pulled to actuate the surgical instrument.

9. The medical system of claim 8, wherein said actuator rod has an adjustable rest position.

10. The medical system of claim 6, wherein said actuator assembly includes an adapter that can couple the surgical instrument to a housing of said actuator assembly.

11. The medical system of claim 6, wherein said cable includes a collar that is captured by a locking arm of said foot pedal.

12. A medical system that can allow a surgeon to manually actuate a surgical instrument, comprising:
   an actuator assembly that can be coupled to the surgical instrument;
   a cable that is coupled to said actuator assembly and which has a collar; and,
   a foot pedal that is coupled to said cable, said foot pedal having a platform which can be moved to move said cable and actuate the surgical instrument, said foot pedal further having a locking arm that captures said collar of said cable.

13. The medical system of claim 12, wherein the actuation of the surgical instrument is proportional to the movement of said platform.

14. The medical system of claim 12, wherein said foot pedal includes an actuator plate that pulls said cable when said platform is depressed.

15. The medical system of claim 12, wherein said actuator assembly includes an actuator rod that is moved when said cable is pulled to actuate the surgical instrument.

16. The medical system of claim 15, wherein said actuator rod has an adjustable rest position.

17. The medical system of claim 12, wherein said actuator assembly includes an adapter that can couple the surgical instrument to a housing of said actuator assembly.

18. A medical system, comprising:
   a surgical instrument;
   an actuator assembly that is coupled to said surgical instrument;
   a cable that is coupled to said actuator assembly; and,
   a foot pedal that is coupled to said cable, said foot pedal having a platform which can be moved to move said cable and actuate said surgical instrument, said foot pedal further having an actuator plate that pulls said cable when said platform is depressed.

19. The medical system of claim 18, wherein the actuation of said surgical instrument is proportional to the movement of said platform.

20. The medical system of claim 18, wherein said actuator assembly includes an actuator rod that is moved when said cable is pulled to actuate said surgical instrument.

21. The medical system of claim 20, wherein said actuator rod has an adjustable rest position.

22. The medical system of claim 18, wherein said actuator assembly includes an adapter that can couple said surgical instrument to a housing of said actuator assembly.

23. The medical system of claim 22, wherein said cable includes a collar that is captured by a locking arm of said foot pedal.

24. A medical system, comprising:

a surgical instrument;

an actuator assembly that has a housing and an adapter that couples said surgical instrument to said housing;

a cable that is coupled to said actuator assembly; and, a foot pedal that is coupled to said cable, said foot pedal having a platform which can be moved to move said cable and actuate said surgical instrument.

25. The medical system of claim 24, wherein the actuation of said surgical instrument is proportional to the movement of said platform.

26. The medical system of claim 24, wherein said foot pedal includes an actuator plate that pulls said cable when said platform is depressed.

27. The medical system of claim 26, wherein said actuator assembly includes an actuator rod that is moved when said cable is pulled to actuate said surgical instrument.

28. The medical system of claim 27, wherein said actuator rod has an adjustable rest position.

29. The medical system of claim 24, wherein said cable includes a collar that is captured by a locking arm of said foot pedal.

30. A medical system, comprising:

a surgical instrument;

an actuator assembly housing;

an adapter that couples said surgical instrument to said actuator assembly housing;

an actuator rod that is coupled to said actuator assembly housing and can be moved to actuate said surgical instrument;

a cable that is coupled to said actuator rod; and, a foot pedal that is coupled to said cable, said foot pedal having a platform which can be moved to move said cable and said actuator rod and actuate said surgical instrument.

31. The medical system of claim 30, wherein the actuation of said surgical instrument is proportional to the movement of said platform.

32. The medical system of claim 30, wherein said foot pedal includes an actuator plate that pulls said cable when said platform is depressed.

33. The medical system of claim 30, wherein said cable includes a collar that is captured by a locking arm of said foot pedal.

34. The medical system of claim 30, wherein said actuator rod has an adjustable rest position.

* * * * *